United States Patent
Lee et al.

(10) Patent No.: US 11,166,898 B2
(45) Date of Patent: Nov. 9, 2021

(54) HUMAN GROWTH HORMONE FUSION PROTEIN WITH ENHANCED THERMAL STABILITY AND COSMETIC COMPOSITION FOR ANTI-WRINKLE AND MAINTAINING SKIN ELASTICITY COMPRISING THE SAME AS EFFECTIVE COMPONENT

(71) Applicants: NEXGEN BIOTECHNOLOGIES, INC., Seoul (KR); Sun Kyo Lee, Gyeonggi-do (KR)

(72) Inventors: Sun Kyo Lee, Gyeonggi-do (KR); Seong Ran Lee, Gyeonggi-do (KR); Han Bong Ryu, Seoul (KR); Tae Won Choi, Seoul (KR); Tae Hyun Kim, Gyeonggi-do (KR)

(73) Assignees: Sun Kyo Lee, Geyonggi-do (KR); NEXGEN BIOTECHNOLOGIES, INC., Seoul (KR)

( * ) Notice: Subject to any disclaimer, the term of this patent is extended or adjusted under 35 U.S.C. 154(b) by 263 days.

(21) Appl. No.: 16/962,139

(22) PCT Filed: Jan. 9, 2017

(86) PCT No.: PCT/KR2017/000238
§ 371 (c)(1),
(2) Date: Jul. 14, 2020

(87) PCT Pub. No.: WO2017/122969
PCT Pub. Date: Jul. 20, 2017

(65) Prior Publication Data
US 2020/0405612 A1 Dec. 31, 2020

(30) Foreign Application Priority Data
Jan. 15, 2016 (KR) .................. 10-2016-0005606

(51) Int. Cl.
| | | |
|---|---|---|
| A61K 8/64 | (2006.01) | |
| A61Q 19/08 | (2006.01) | |
| A61Q 19/10 | (2006.01) | |
| C07K 14/61 | (2006.01) | |
| A61K 8/02 | (2006.01) | |
| A61Q 19/00 | (2006.01) | |

(52) U.S. Cl.
CPC .............. *A61K 8/64* (2013.01); *A61K 8/0212* (2013.01); *A61Q 19/007* (2013.01); *A61Q 19/08* (2013.01); *A61Q 19/10* (2013.01); *C07K 14/61* (2013.01)

(58) Field of Classification Search
CPC ...... A61K 8/0212; A61K 8/64; A61Q 19/007; A61Q 19/08; A61Q 19/10; C07K 14/43518; C07K 14/61; C12N 15/52; C12N 15/62; C12N 15/63
See application file for complete search history.

(56) References Cited

U.S. PATENT DOCUMENTS

| | | | |
|---|---|---|---|
| 7,846,445 B2 * | 12/2010 | Schellenberger .. | G01N 33/6845 424/180.1 |
| 8,703,717 B2 * | 4/2014 | Schellenberger ...... | A61K 47/64 514/21.2 |
| 2013/0065278 A1 | 3/2013 | Johansson et al. | |
| 2014/0024806 A1 | 1/2014 | Kieliszewski et al. | |

FOREIGN PATENT DOCUMENTS

| | | |
|---|---|---|
| EP | 2 644 619 A1 | 10/2013 |
| KR | 10-2015-0056021 A | 5/2015 |
| KR | 10-1565542 B1 | 11/2015 |
| KR | 10-1652953 B1 | 8/2016 |

OTHER PUBLICATIONS

International Search Report for PCT/KR2017/000238 dated Apr. 4, 2017.
Silvia Gomes et al., "Natural and genetically engineered proteins for tissue engineering", Progress in Polymer Science vol. 37, pp. 1-17, 2012.
Kristina Spiess et al., "Recombinant Spider Silk Proteins for Applications in Biomaterials", Macromol. Biosci. vol. 10, pp. 998-1007, 2010.
Douglas Hanahan, "Studies on Transformation of *Escherichia coli* with Plasmids", J. Mol. Biol. vol. 166, pp. 557-580, 1983.
Filippo Mulinacci et al., "Influence of methionine oxidation on the aggregation of recombinant human growth hormone", European Journal of Pharmaceutics and Biopharmaceutics, vol. 85, pp. 42-52, 2013.

* cited by examiner

*Primary Examiner* — Julie Ha
(74) *Attorney, Agent, or Firm* — The PL Law Group, PLLC

(57) ABSTRACT

A human growth hormone fusion protein has enhanced thermal stability. The human growth hormone fusion protein has the amino acid sequence SEQ ID NO: 3 or SEQ ID NO: 4. A gene encoding the human growth hormone fusion protein has *E. coli* codon-optimized nucleotide sequence of SEQ ID NO: 5 or SEQ ID NO: 6. A recombinant vector includes the aforementioned gene. A host cell is transformed with the aforementioned recombinant vector. A method for producing in a host cell a human growth hormone fusion protein includes transforming a host cell with the aforementioned recombinant vector. The human growth hormone fusion protein may improve skin wrinkle and maintain skin elasticity. As the human growth hormone fusion protein has thermal stability and also has an effect of improving skin wrinkle and increasing the effect of maintaining skin elasticity, it can be advantageously used as a raw material of cosmetics.

5 Claims, 7 Drawing Sheets
Specification includes a Sequence Listing.

HUMAN GROWTH HORMONE FUSION PROTEIN WITH ENHANCED THERMAL STABILITY AND COSMETIC COMPOSITION FOR ANTI-WRINKLE AND MAINTAINING SKIN ELASTICITY COMPRISING THE SAME AS EFFECTIVE COMPONENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/000238, filed Jan. 9, 2017, which claims priority to the benefit of Korean Patent Application No. 10-2016-0005606 filed in the Korean Intellectual Property Office on Jan. 15, 2016, the entire contents of which are incorporated herein by reference.

TECHNICAL FIELD

The present invention relates to a human growth hormone fusion protein with enhanced thermal stability and a cosmetic composition for improving skin wrinkle and maintaining skin elasticity comprising the same as an effective component.

BACKGROUND ART

Human growth hormones have effects on many organs in human body, including skeletal development, muscle development, fat breakdown, organ development, sexual maturation, and the like. Human growth hormones are generally provided in the form of an injection solution and used as a pharmaceutical product for strengthening cardiovascular system, improving workout performances, strengthening muscle, or the like. In particular, they have been proved to be effective for improving the body metabolism including breaking down fat, ameliorating arthritis, increasing skin thickness, improving cardiopulmonary performance, increasing muscle mass, and the like, and also maintaining skin with good elasticity. Accordingly, it has been also known that the growth hormones are highly effective for preventing aging.

Maximal growth hormone secretion occurs in puberty. Although the hormone level starts to decrease slowly after age 20, it remains quite high until age 40. However, after age 60, it drops to 50% or lower of the 20s' level. Low growth hormone level causes less skin elasticity due to a decrease in skin thickness and skin collagen, in particular, increased fine lines and wrinkles around the eye and mouth. In this regard, growth hormones are used for representative drug therapy for preventing the aging process.

The growth hormones play a key role in maintaining skin elasticity like wrinkle improvement as well as treating a cardiovascular disorder. As such, they can be used not only for skin cosmetics but also for skin care to prevent the aging.

Spider dragline protein has spidroin as a main component, and it is a protein fiber produced by a spider. There are seven kinds of the silk protein. The dragline silk, which is the strongest among the spider silk proteins, has tensile strength that is comparable to that of Kevlar as p-aramid fiber. It is also known that the flagellum-like silk has the elasticity that is almost two times higher than the dragline silk.

Like cellulose, the spider silk protein has a structure with repeated motifs of amino acids such as glycine or alanine, and most of the corresponding nucleotide sequences are found from the β-sheet regions of swollen silk. In the fiber, those β-sheet regions form a structure which connects the crystal parts and provide the silk protein with high tensile strength. Pyrrolidine component in spider dragline has a hygroscopic property and maintains simultaneously the moistness in spider dragline. Potassium hydrogen phosphate generates protons in aqueous solution to induce the acidification of silk, and thus it plays a role of protecting the spider dragline from molds and bacteria. Those characteristics of spider silk protein are believed to be useful as a new raw material for replacing high molecular-weight collagen, which is broadly used as a raw material of cosmetics for skin moisturization and maintaining of skin elasticity.

In the present invention, studies are made to develop a new protein for more efficiently maintaining the wrinkle-improving effect and anti-aging effect of human growth hormone, in particular, for maintaining skin elasticity, and, as a result, it was found that the thermal stability of human growth hormone can be enhanced by using the human growth hormone fused with spider dragline protein so that the wrinkle improvement and maintaining of skin elasticity can be increased to the maximum level.

Meanwhile, in Korean Patent Application Publication No. 2015-0056021, "Cosmetic composition for skin improvement comprising fusion protein of human growth hormone using peptide for promoting skin permeation" is disclosed. Furthermore, in Korean Patent Registration No. 1565542, "Cosmetic composition for skin lifting and anti-aging comprising extract of spider dragline" is disclosed. However, no description has been made for the fusion protein of human growth hormone with enhanced thermal stability and cosmetic composition for improving skin wrinkle and maintaining skin elasticity comprising the same as an effective component as they are disclosed in the present invention.

SUMMARY

The present invention is devised in view of the circumstances described above, and according to fusion of human growth hormone protein to a spider silk protein, the inventors of the present invention produced a novel fusion protein of human growth hormone with enhanced thermal stability. The human growth hormone fusion protein can promote skin cell growth and it also exhibits, as a result of producing various cosmetic formulations (e.g., skin, essence, lotion, and crème) by having the fusion protein as an effective component and carrying out a skin test, the effect of improving skin wrinkle and maintaining skin elasticity of a test subject. The present invention is completed accordingly.

To solve the problems described above, the present invention provides a human growth hormone fusion protein with enhanced thermal stability which consists of the amino acid sequence of SEQ ID NO: 3 or SEQ ID NO: 4.

The present invention further provides a gene encoding the aforementioned human growth hormone fusion protein with enhanced thermal stability.

The present invention further provides a recombinant vector comprising the aforementioned gene.

The present invention further provides a host cell transformed with the aforementioned recombinant vector.

The present invention further provides a method for producing in a host cell a human growth hormone fusion protein with enhanced thermal stability by transforming a host cell with the aforementioned recombinant vector.

The present invention still further provides a cosmetic composition for improving skin wrinkle and maintaining skin elasticity comprising, as an effective component, a human growth hormone fusion protein with enhanced thermal stability which consists of the amino acid sequence of SEQ ID NO: 3 or SEQ ID NO: 4.

The method of production in *E. coli* (*Escherichia coli*) using *E. coli* codon-optimized gene encoding the human growth hormone fusion protein of the present invention has a simplified production process as the proteins are expressed in the form of an inclusion body in *E. coli* and allows large-scale production of proteins. Furthermore, as the human growth hormone fusion protein fused with spider silk protein which is produced by the aforementioned method has, in addition to the enhanced thermal stability, an excellent anti-aging function based on improvement of skin wrinkle and maintaining of skin elasticity, it is expected that the fusion protein can be advantageously used as a raw material of functional cosmetics.

DETAILED DESCRIPTION

Figure 1:
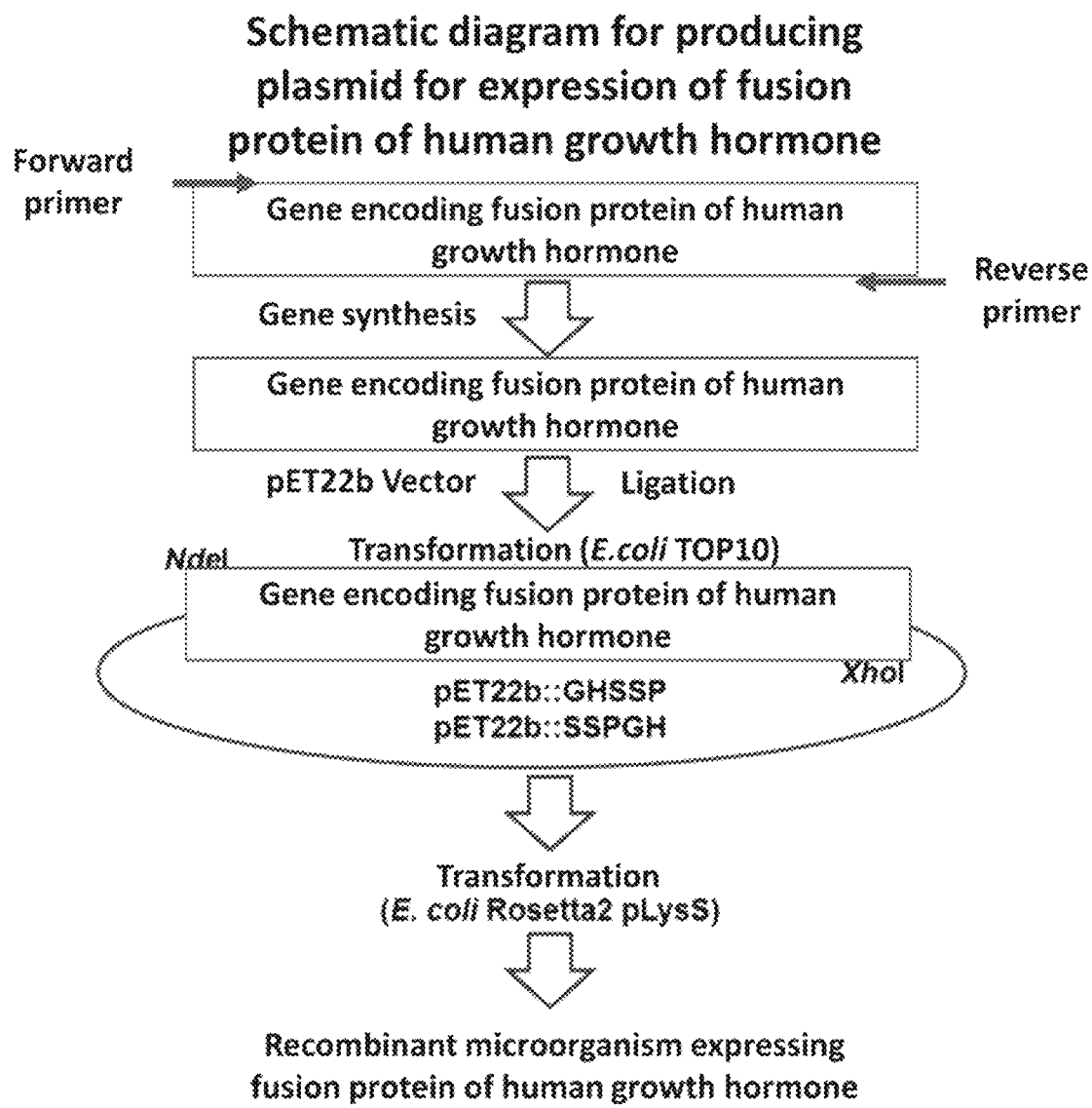
FIG. 1 is a schematic drawing illustrating the process for preparing the recombinant plasmid (pET22b::GHSSP and pET22b::SSPGH) which includes a gene encoding the human growth hormone fusion protein, and transforming *E. coli* with the plasmid.

To achieve the object of the present invention, the present invention provides a human growth hormone fusion protein with enhanced thermal stability which consists of the amino acid sequence of SEQ ID NO: 3 or SEQ ID NO: 4.

The human growth hormone fusion protein with enhanced thermal stability of the present invention is a novel protein which is produced by fusion of the spider silk protein consisting of the amino acid sequence of SEQ ID NO; 1 to the amino terminal or carboxy terminal of human growth hormone consisting of the amino acid sequence of SEQ ID NO: 2.

The scope of the human growth hormone fusion protein with enhanced thermal stability according to the present invention includes a protein having the amino acid sequence of SEQ ID NO: 3 (i.e., spider silk protein is fused to the amino terminal of human growth hormone protein) or the amino acid sequence of SEQ ID NO: 4 (i.e., spider silk protein is fused to the carboxy terminal of human growth hormone protein), and also functional equivalents of those proteins. The term "functional equivalent" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 3 or SEQ ID NO: 4, and it indicates a protein exhibiting substantially the same activity as the protein represented by SEQ ID NO: 3 or SEQ ID NO: 4. The expression "substantially the same activity" means an activity of improving skin wrinkle and maintaining skin elasticity while having thermal stability.

The present invention further provides a gene encoding the human growth hormone fusion protein with enhanced thermal stability. This gene may consist of a nucleotide sequence of *E. coli* codon-optimized SEQ ID NO: 5 or SEQ ID NO: 6, but it is not limited thereto.

The gene encoding the human growth hormone fusion protein with enhanced thermal stability of the present invention may include the nucleotide sequence of SEQ ID NO: 5 (i.e., gene encoding a protein in which spider silk protein is fused to the amino terminal of human growth hormone protein) or the nucleotide sequence of SEQ ID NO: 6 (i.e., gene encoding a protein in which spider silk protein is fused to the carboxy terminal of human growth hormone protein). Further, homologues of the nucleotide sequence are also within the scope of the present invention. Specifically, the above-described gene may comprise a nucleotide sequence which has preferably at least 70%, more preferably at least 80%, still more preferably at least 90%, and most preferably at least 95% homology with the nucleotide sequence selected from a group consisting of nucleotide sequences of SEQ ID NO: 5 and SEQ ID NO: 6. The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

"Codon optimization" means a modification of codon of a polynucleotide encoding a protein with a codon that is used first than others in a specific organism such that the coded protein can be more efficiently expressed therein. Because most amino acids are described by several codons that are referred to as "synonym" or "synonymous codon", genetic codes have degeneracy. However, codon usage by a specific organism is not random, and it is rather biased to specific codon triplets. Such codon usage bias may be even higher in relation with a certain gene, a gene with common function or ancestor origin, protein expressed at high level vs. proteins with low copy number, or a group protein coding region of a genome of an organism. The nucleotide sequence of SEQ ID NO: 5 or SEQ ID NO: 6 of the present invention is a sequence which has been optimized to *E. coli* codon such that the gene encoding spider silk protein and human-derived growth hormone protein can be expressed well in *E. coli*.

The present invention further provides a recombinant vector comprising the gene encoding the human growth hormone fusion protein with enhanced thermal stability, and a host cell transformed with the recombinant vector.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

According to the present invention, the gene encoding the human growth hormone fusion protein with enhanced thermal stability can be inserted to a recombinant expression vector. The term "recombinant expression vector" means bacteria plasmid, phage, yeast plasmid, plant cell virus, mammalian cell virus, or other vector. Any plasmid and vector can be generally used if it can replicate and is stabilized in a host. Important characteristics of the expression vector include that it comprises a replication origin, a promoter, a marker gene, and a translation control element.

The expression vector comprising the gene sequence encoding the human growth hormone fusion protein with enhanced thermal stability and an appropriate signal for regulating transcription/translation can be constructed according to a method that is well known to a skilled person in the art. The method includes an in vitro recombinant DNA technique, a DNA synthesis technique, and an in vivo recombinant technique. For inducing mRNA synthesis, the DNA sequence can be effectively linked to a suitable promoter present in the expression vector. In addition, the expression vector may comprise a ribosome binding site as a translation initiation site and a transcription terminator.

The recombinant vector according to one embodiment of the present invention is prepared by in-frame fusion of the synthesized gene encoding the human growth hormone fusion protein (SEQ ID NO: 5 or SEQ ID NO: 6) to 5' terminal (NdeI restriction enzyme site) and 3' terminal (XhoI restriction enzyme site) of pET22b vector, and it is a vector characterized in that it can produce the human growth hormone fusion protein based on effective expression of the aforementioned gene with an aid of lac promoter (lac promoter) and lacI repressor (lacI repressor).

For a host cell having an ability of having stable and continuous cloning and expression of the vector of the present invention in a prokaryotic cell, any host cell known in the pertinent art can be used. Examples thereof include, *Bacillus* sp. strain including *E. coli* Rosetta, *E. coli* JM109, *E. coli* BL21, *E. coli* RR1, *E. coli* LE392, *E. coli* B, *E. coli* X 1776, *E. coli* W3110, *Bacillus subtillus, Bacillus thuringiensis* and the like, and intestinal bacteria and strains including *Salmonella typhimurium, Serratia marcescens* and various *Pseudomonas* sp. etc.

Furthermore, when an eukaryotic cell is transformed with the vector of the present invention, yeast (*Saccharomyce cerevisiae*), an insect cell, a human cell (for example, CHO (Chinese hamster ovary) cell line, W138, BHK, COS-7, 293, HepG2, 3T3, RIN, and MDCK cell line), a plant cell, and the like can be used as a host cell.

The host cell transformed with the recombinant vector according to one embodiment of the present invention can be preferably *E. coli*, and more preferably *E. coli* Rosetta2 (DE3) pLysS, but it is not limited thereto.

When a host cell is a prokaryotic cell, delivery of the recombinant vector of the present invention into a host cell can be carried out by $CaCl_2$ method, Hanahan's method (Hanahan, D., J. Mol. Biol., 166:557-580 (1983)) or an electroporation method, and the like. In addition, when a host cell is an eukaryotic cell, the vector can be introduced to a host cell by a microinjection method, calcium phosphate precipitation method, an electroporation method, a liposome-mediated transfection method, DEAE-dextran treatment method, or a gene bombardment method, and the like.

The present invention further provides a method for producing in a host cell a human growth hormone fusion protein including overexpressing a gene encoding a human growth hormone fusion protein by transforming a host cell with the recombinant vector of the present invention.

In the method according to one embodiment of the present invention, the host cell can be preferably *E. coli*, and more preferably *E. coli* Rosetta2 (DE3) pLysS, but it is not limited thereto.

The present invention still further provides a cosmetic composition for improving skin wrinkle and maintaining skin elasticity comprising, as an effective component, a human growth hormone fusion protein which consists of the amino acid sequence of SEQ ID NO: 3 or SEQ ID NO: 4.

In the cosmetic composition according to one embodiment of the present invention, content of the human growth hormone fusion protein may be 0.000001 to 0.002% by weight relative to the total weight of the cosmetic composition, but it is not limited thereto.

In the cosmetic composition of the present invention, components that are typically used for a cosmetic composition are included in addition to the effective components that are described above. Examples thereof include a lipid material, an organic solvent, a dissolution agent, a condensation agent, a gelling agent, a softening agent, an antioxidant, a suspension agent, a stabilizer, a foaming agent, an aroma, a surface active agent, water, an ionic or non-ionic emulsifier, a filler, a metal ion sequestering agent, a chelating agent, a preservative, vitamin, a blocking agent, a moisturizing agent, essential oil, a dye, a pigment, a hydrophilic or lipophilic activating agent, a common auxiliary agent such as lipid vesicle, and a carrier.

The composition of the present invention can be prepared in any formulation that is generally prepared in the pertinent art. For example, the composition may be formulated into a solution, a suspension, an emulsion, a paste, a gel, a crème, a lotion, a powder, an oil, a powder foundation, an emulsion foundation, a wax foundation, a spray, or the like, but it is not limited thereto. More specifically, the composition may be formulated into a skin, a skin softener, a skin toner, an astringent, a lotion, a milk lotion, a moisture lotion, a nutrition lotion, a massage crème, a nutrition crème, an eye crème, a moisture crème, a hand crème, an essence, a nutrition essence, a pack, a cleansing foam, a cleansing water, a cleansing lotion, a cleansing crème, a body lotion, a body cleanser, a soap, a powder, or the like.

In a case in which the cosmetic composition of the present invention has a formulation type of paste, crème, or gel, it is possible to use, as a carrier component, animal oil, plant oil, wax, paraffin, starch, tragacanth, cellulose derivatives, polyethylene glycol, silicone, bentonite, silica, talc, or zinc oxide.

In a case in which the cosmetic composition of the present invention has a formulation type of powder or spray, it is possible to use, as a carrier component, lactose, talc, silica, aluminum hydroxide, calcium silicate, or polyamide powder. In particular, in a case in which the cosmetic composition is a spray, a propellant such as chlorofluorohydrocarbon, propane/butane, or dimethyl ether may be additionally included.

In a case in which the cosmetic composition of the present invention has a formulation type of solution or emulsion, a solvent, a dissolution agent, or an emulsifier is used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

In a case in which the cosmetic composition of the present invention has a formulation type of suspension, it is possible to use, as a carrier component, a liquid phase diluent such as water, ethanol, or propylene glycol, a suspension agent such as ethoxylated isostearyl alcohol, polyoxyethlyene sorbitol ester, or polyoxyethylene sorbitan ester, microcrystalline cellulose, aluminum metahydroxide, bentonite, agar, or tragacanth.

Hereinbelow, the present invention is explained in greater detail in view of the Examples. However, it is evident that the following Examples are given only for exemplification of the present invention and by no means the present invention is limited to the following Examples.

EXAMPLES

Example 1

Preparation of Recombinant Expression Vector and Transformed Recombinant Microorganism for Producing Human Growth Hormone Fusion Protein The optimized gene encoding the fusion protein of human growth hormone (hereinbelow, "GH"), recombinant expression vector, and transformed recombinant microorganism were prepared in accordance with the following methods.

By using as a template the genes encoding the human growth hormone and spider silk protein (hereinbelow, "SSP"), which is used as a partner protein, the gene (SEQ ID NO: 5 and SEQ ID NO: 6) fragments encoding human growth hormone fusion protein, which consist of 305 amino acids and are optimized for expression in a host microorganism were prepared by synthesis.

To synthesize the gene encoding a fusion protein having the water-soluble spider silk protein bound to the amino terminal (N-terminal) of human growth hormone, 315 nucleotides encoding the water-soluble spider silk protein, which have been optimized for $E.$ $coli$, were synthesized by using a forward primer (1) (5'-AAGGAGATATA-CATATGCAAGGTGCTGGTGCTGCCG-3', SEQ ID NO: 7) and a reverse primer (1) (5'-CAGCGGAATAGTGGG-GAATGCGCCTGCTCCCTGTCC-3', SEQ ID NO: 8). Furthermore, 579 nucleotides encoding the human growth hormone, which have been optimized for $E.$ $coli$, were synthesized by using a forward primer (2) (5'-GGACAGG-GAGCAGGCGCATTCCCCACTATTCCGCTG-3', SEQ ID NO: 9) and a reverse primer (2) (5'-GGTGGTGGTGCTCGAGAAAGCCGCAG-GAACCCTCG-3', SEQ ID NO: 10). By having each of the genes encoding the water-soluble silk spider protein or human growth hormone, which have been synthesized by the above method, as a template and also by using a forward primer (1) and a reverse primer (2), a gene consisting of 897 nucleotides encoding a fusion protein having the water-soluble spider silk protein bound to the N-terminal of the human growth hormone was finally synthesized according to polymerase chain reaction (PCR).

To synthesize the gene encoding a fusion protein having the water-soluble spider silk protein bound to the carboxy terminal (C-terminal) of human growth hormone, a gene consisting of 897 nucleotides, which encodes a fusion protein having the spider silk protein bound to the C-terminal of the human growth hormone, was synthesized in the same manner as the method for synthesizing a gene encoding a fusion protein having the spider silk protein bound to the N-terminal of the human growth hormone, by using a forward primer (3) (5'-AAGGAGATATACATATGTTCCC-CACTATTCCG-3', SEQ ID NO: 11) and a reverse primer (3) (5'-CGGCAGCACCAGCACCTTGAAAGCCGCAG-GAACCCTCG-3', SEQ ID NO: 12), and a forward primer (4) (5'-CGAGGGTTCCTGCGGCTTT-CAAGGTGCTGGTGCTGCCG-3', SEQ ID NO: 13) and a reverse primer (4) (5'-GGTGGTGGTGCTCGAGTGCGCCTGCTCCCTGTCC-3', SEQ ID NO: 14).

The aforementioned gene fragments and recombinant plasmid were digested with the same restriction enzymes (5' terminal NdeI and 3' terminal XhoI) followed by insertion, and thus the recombinant plasmid pET22b::GHSSP and pET22b::SSPGH) shown in FIG. 1 was prepared. Then, $E.$ $coli$ TOP10 was transformed with each of the prepared recombinant plasmid to obtain a large amount of the gene construct from the host microorganism. In addition, $E.$ $coli$ Rosetta2 (DE3) pLysS (Novagen, Germany) was transformed with the prepared recombinant plasmid to produce a recombinant microorganism for producing a human growth hormone fusion protein, in which the gene construct is inserted to a host microorganism.

Example 2

Expression Induction, Isolation, and Purification of Human Growth Hormone Fusion Protein $E.$ $coli$ Rosetta2 (DE3) pLysS prepared in Example 1 was cultured in 1 L LB medium or BSB medium till to have $OD_{600}$=0.6 to 0.8 for batch culture, or $OD_{600}$=15 to 20 for continuous culture using 20 L fermentation apparatus. After that, by adding 1 to 5 mM IPTG or 2% lactose (both in final concentration) to each cell culture medium, expression of recombinant $E.$ $coli$ was induced. After gene expression induction, the cells were further cultured for 3 to 4 hours, and then collected by centrifuge. The collected cells were sufficiently suspended in a buffer solution (phosphate buffered saline, 8 g of NaCl, 0.2 g of KCl, 1.44 g of $Na_2HPO_4$, and 0.24 g of $KH_2PO_4$/l, pH 7.4) and disrupted using an ultrasonic cell homogenizer. As a result, a solution containing intracellular proteins was isolated.

Figure 2:
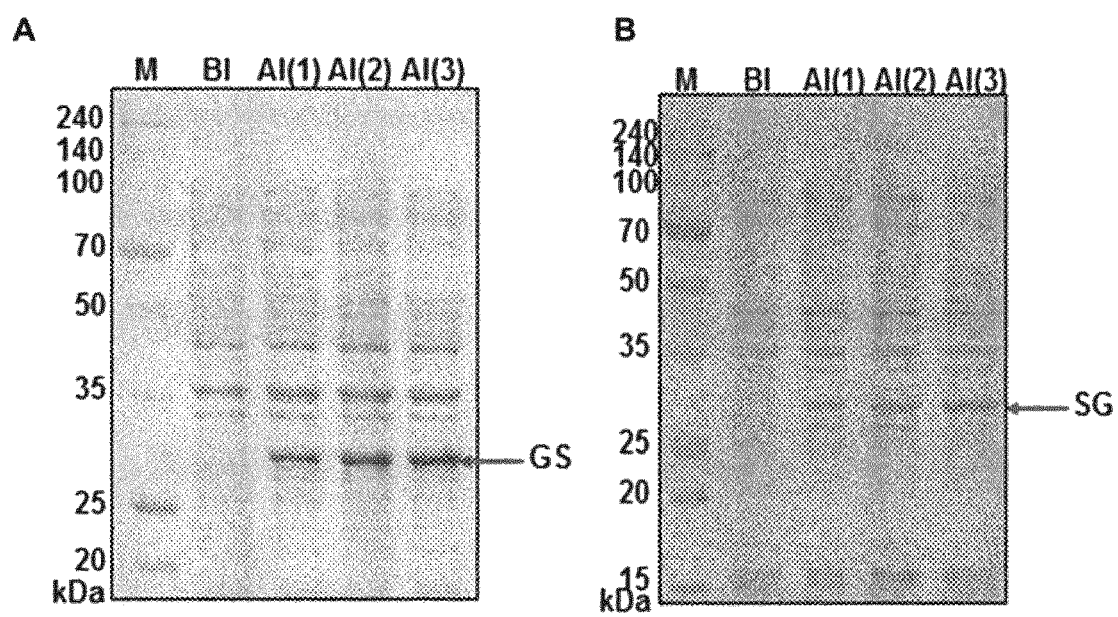
FIG. 2 shows the results of performing electrophoresis on SDS-polyacrylamide gel to determine the presence or absence of the expression of human growth hormone fusion protein in *E. coli*. A of FIG. 2 shows the result of determining the expression of human growth hormone fusion protein fused with spider silk protein at the carboxy terminal, and B of FIG. 2 shows the result of determining the expression of human growth hormone fusion protein fused with spider silk protein at the amino terminal. In the figure, abbreviations are as follows: M; size marker, BI; crude cell lysate before inducing expression, AI (number); crude cell lysate (time) after inducing expression, GS; fusion protein of human growth hormone-spider silk protein, SG; fusion protein of spider silk protein-human growth hormone.

By using the above isolated solution as a sample, protein expression was examined by 15% SDS-polyacrylamide gel electrophoresis. As a result, expression of the human growth hormone fusion protein was shown from the crude cell lysate in which the expression induction has been carried out with IPTG or lactose (FIG. 2).

In order to isolate and purify the human growth hormone fusion protein of which expression has been shown from above, the inclusion body was solubilized using a solubilizing buffer solution (5M urea, pH 11), and then subjected to a refolding process using ultrafine filtration (0.45 μm fine filtration membrane, and 1K ultrafine filtration membrane). Accordingly, the fusion protein of human growth hormone-spider silk protein (GS) and fusion protein of spider silk protein-human growth hormone (SG) were finally isolated by using a storage buffer solution (phosphate buffered saline, PBS).

Figure 3:
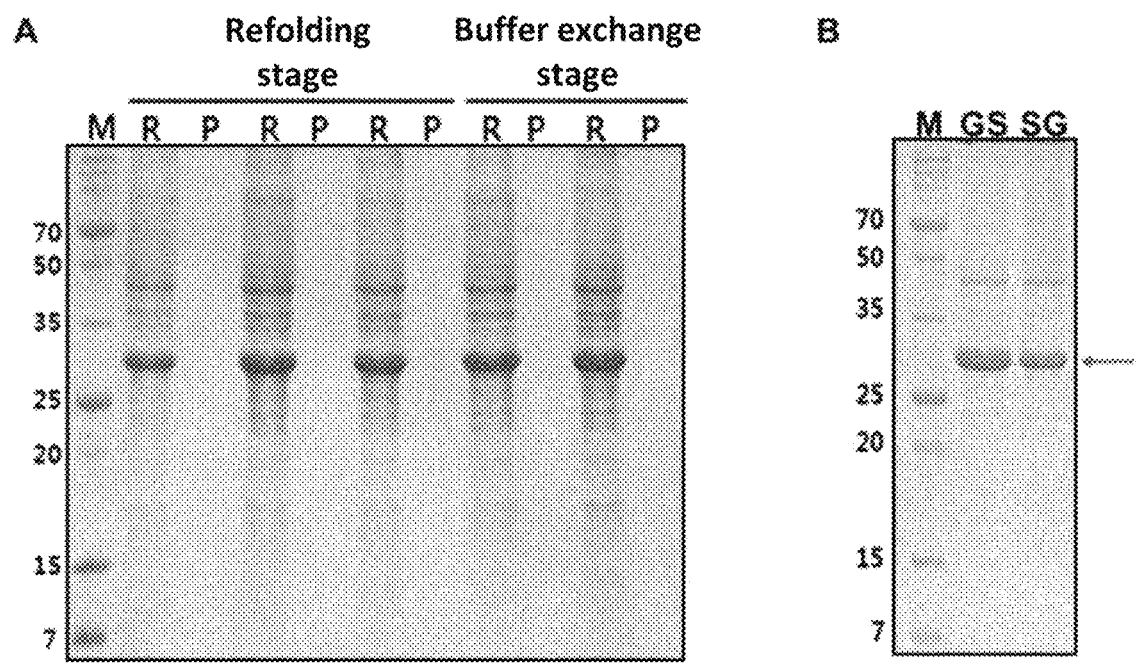
FIG. 3 shows the result of SDS-polyacrylamide gel electrophoresis to determine the isolation and purification process of the human growth hormone fusion protein. A of FIG. 3 shows the result of determining the isolation level of the fusion protein during refolding stage and buffer exchange stage, and B of FIG. 3 shows the electrophoresis result of the fusion protein which has been finally isolated by nickel-agarose column. In the figure, abbreviations are as follows: M; size marker, R; refolding sample (i.e., dialysis retentate), P; refolding sample (permeate), GS; fusion protein of human growth hormone-spider silk protein; SG, fusion protein of spider silk protein-human growth hormone.

For complete purification of the above fusion protein, the isolated fusion protein was passed through a nickel-agarose column at a rate of 1 to 3 ml/minute. Subsequently, the column was washed several times with a binding buffer solution, and by adding 50, 100, and 250 mM imidazole solution (pH 7.4) to the column, the fusion protein of human growth hormone-spider silk protein (GS) and fusion protein of spider silk protein-human growth hormone (SG) were fractionated in a portion of 1 ml and eluted from the column. Then, the imidazole present in the buffer was removed by using 10 mM potassium phosphate buffer, and thus the fusion protein was finally purified in pure state. To determine the result, 15% SDS-acrylamide gel electrophoresis was carried out. As a result, the finally purified fusion protein was identified with near expected size (i.e., about 30 to 31 kDa) (FIG. 3).

Example 3

Measurement of Activity of Fusion Protein of Human Growth Hormone-Spider Silk Protein (Gs)—Dermal Fibroblast Proliferation Effect With selection of a sample from which the presence of isolated and purified fusion protein of human growth hormone-spider silk protein (GS) has been confirmed as described in Example 2, activity of the fusion protein was measured.

After culturing dermal fibroblast (Human Dermal Fibroblasts adult, HDFa cell), the cells were treated with the fusion protein at concentration of 0, 0.02 ppm, 0.2 ppm, 2 ppm or 20 ppm followed by culture for 3 days at 37° C. Thereafter, proliferation of the dermal fibroblast was determined based on crystal violet staining.

Figure 4:
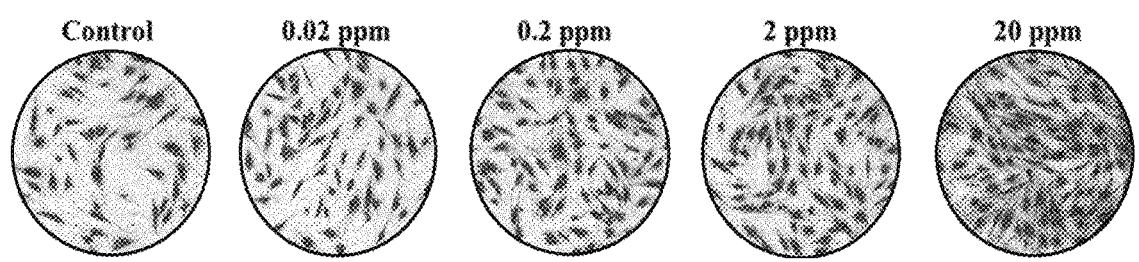
FIG. 4 is a photographic image in which the dermal fibroblast proliferation effect after the treatment of dermal fibroblast with fusion protein of human growth hormone-spider silk protein (GS) is shown by crystal violet staining.

As a result, it was found that, compared to the non-treatment control group (0 ppm), a more favorable dermal fibroblast proliferation effect is obtained as the concentration of the fusion protein increases (0.2 to 20 ppm) (FIG. 4).

Example 4

Thermal Stability Analysis of Fusion Protein

With selection of a sample from which the presence of isolated and purified fusion protein of human growth hormone-spider silk protein has been confirmed as described in Example 2, the thermal stability was compared with human growth hormone protein not fused with any spider silk protein. For the thermal stability test, dermal fibroblast was treated with the human growth hormone protein or fusion protein of human growth hormone-spider silk protein at a concentration of 1 ppm, which has been subjected to either gamma ray sterilization (irradiation of 35 kgray) or high-pressure sterilization (treatment at 121° C. for 15 minutes), followed by culture for 3 days at 37° C. Then, cell proliferation degree depending on the protein treatment was determined based on crystal violet staining.

Figure 5:
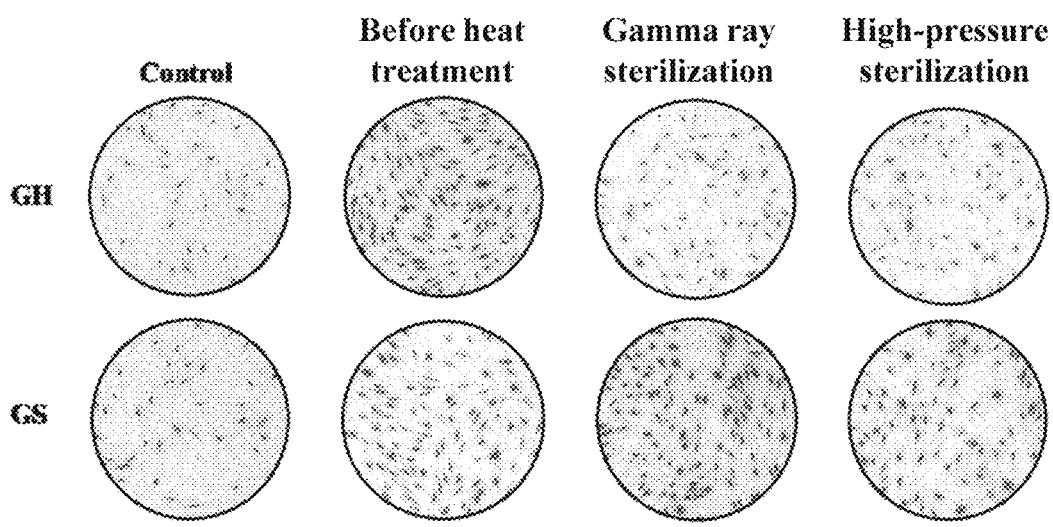
FIG. 5 is a photographic image in which the presence or absence of dermal fibroblast proliferation after the treatment of dermal fibroblast with human growth hormone (GH) or fusion protein of human growth hormone-spider silk protein (GS), which have been subjected to either gamma ray sterilization or high-pressure sterilization, is shown for determination of thermal stability of the fusion protein, in which the dermal fibroblast cell proliferation was examined by crystal violet staining.

As a result, it was found that, compared to the control in which the protein has not been treated, a significant cell proliferation was shown from the group in which human growth hormone (GH) protein has not been given with any heat treatment (i.e., group before heat treatment). However, from the protein treatment group to which gamma ray sterilization or high-pressure sterilization has been carried out, the cell proliferation was found to be less than the "pre-heat treatment" test group. On the other hand, in case of the fusion protein of human growth hormone-spider silk protein (GS), even the test group treated with the fusion protein obtained after gamma ray sterilization or high-pressure sterilization showed cell proliferation that is at the same level or higher level than the group not given with any heat treatment (FIG. 5)

Based on the above result, it was found that the fusion protein of the present invention maintains the protein activity even after a heat treatment, and the fusion protein of the present invention with enhanced thermal stability is believed to be very advantageously used particularly for producing a preservative-free cosmetic product which is produced by using a heat treatment method.

Example 5

Measurement of Activity of Fusion Protein of Human Growth Hormone-Spider Silk Protein (GS)—Cell Proliferation, Wound Healing, and Cell Adhesion Effect in HaCaT Cells With selection of a sample from which the presence of isolated and purified fusion protein of human growth hormone-spider silk protein (GS) has been confirmed as described in Example 2, activity of the fusion protein was measured. The measurement of the activity of fusion protein was carried out by culturing HaCaT cells, treating the cultured cells with the fusion protein at a concentration of 0, 0.02 ppm, 0.2 ppm, 2 ppm and 20 ppm, and analyzing the cell proliferation, wound healing, and cell adhesion in the cultured cells.

Figure 6:
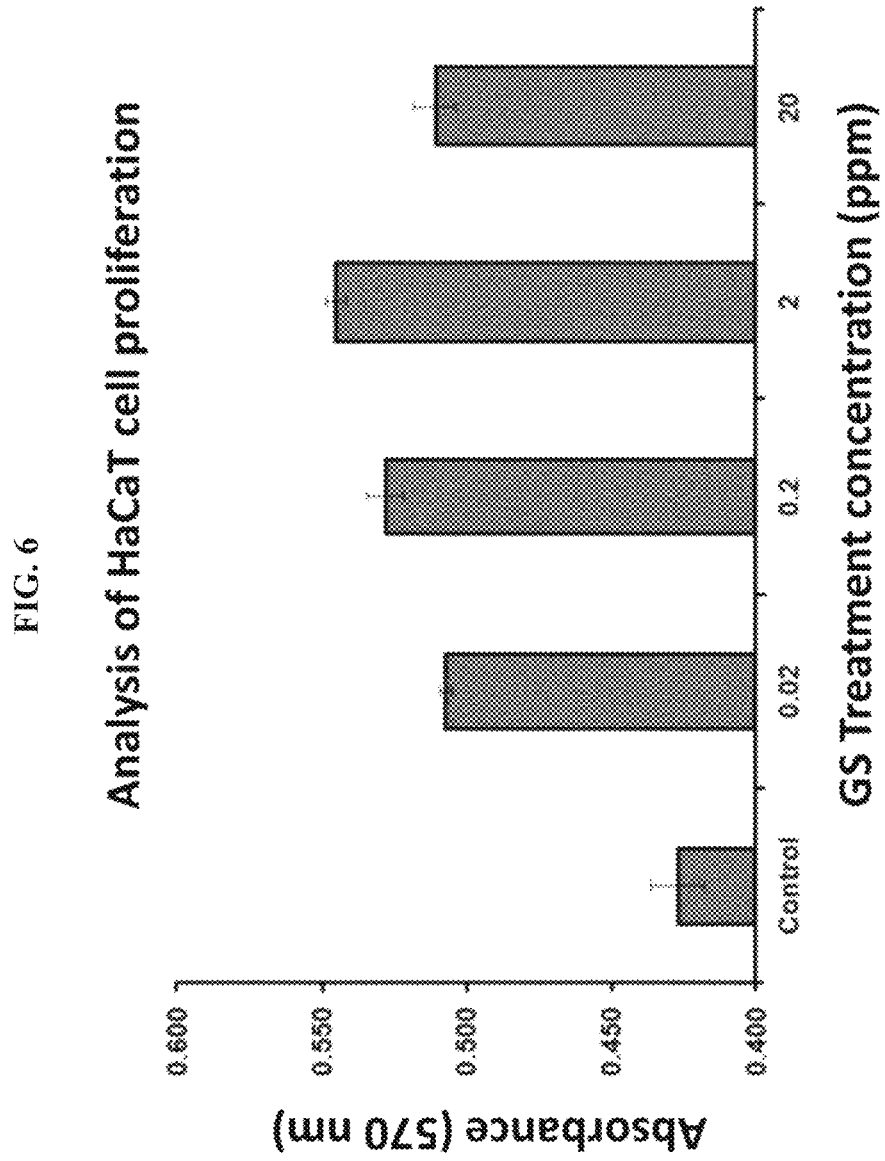
FIG. 6 shows the result of determining the HaCaT cell proliferation effect after treatment of HaCaT cells with the fusion protein of human growth hormone-spider silk protein.

First, when cell proliferation analysis was made by using PRESTOBLUE™ Cell Viability reagent (Invitrogen, USA), HaCaT cell proliferation effect caused by a treatment of the human growth hormone fusion protein was shown (FIG. 6). In particular, an excellent cell proliferation effect was observed when the treatment was carried out at a concentration of 0.2 to 2 ppm.

Figure 7:
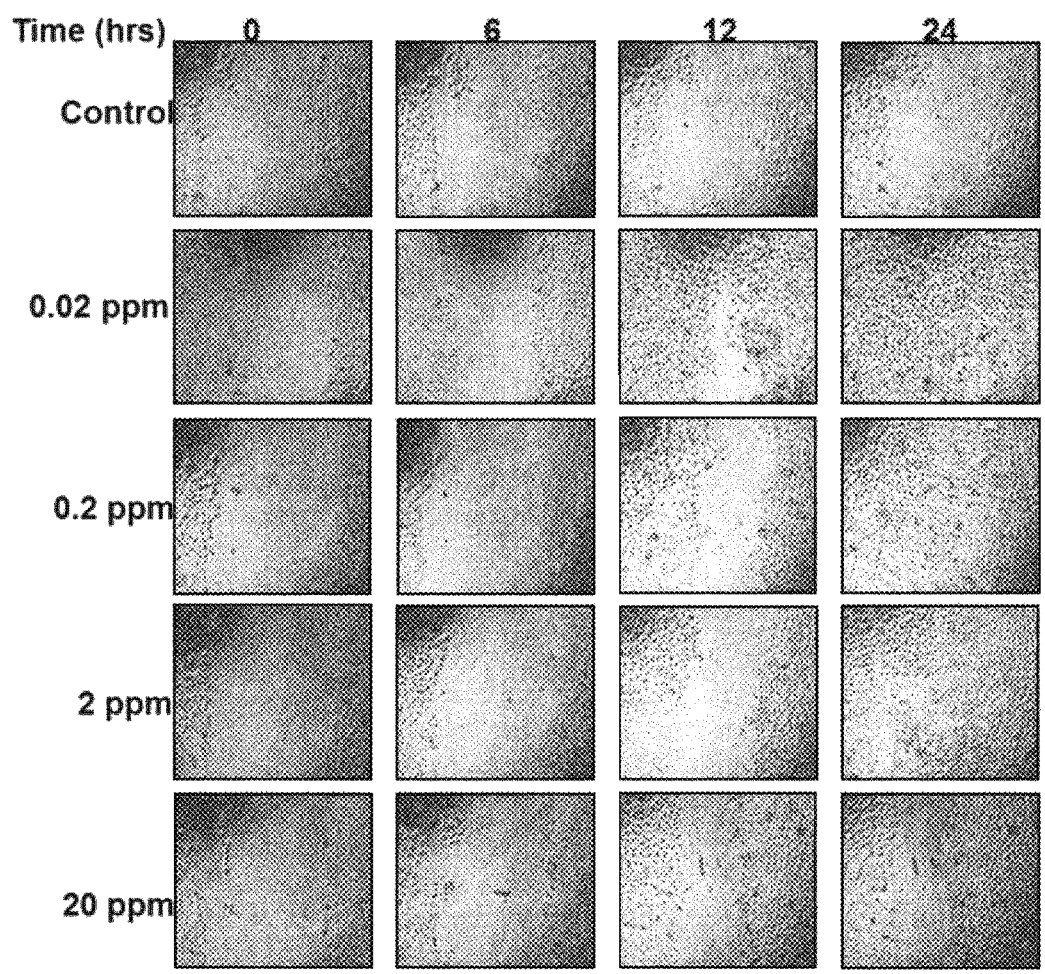
FIG. 7 is a photographic image showing the result of observing the wound healing effect in HaCaT cells after treatment of HaCaT cells with the fusion protein of human growth hormone-spider silk protein.

After culturing HaCaT cells in a well, the human growth hormone fusion protein was added thereto at a concentration of 0, 0.02 ppm, 0.2 ppm, 2 ppm or 20 ppm. Thereafter, the cells were observed every 6 hours by a microscope (Olympus CK40, Olympus, Japan) to examine the wound healing effect in HaCaT cells. Compared to the non-treatment control group (i.e., no treatment with fusion protein), the HaCaT cells treated with the human growth hormone fusion protein showed a wound healing effect, and the effect was found to be particularly strong at a concentration of 0.02 to 0.2 ppm (FIG. 7).

Figure 8:
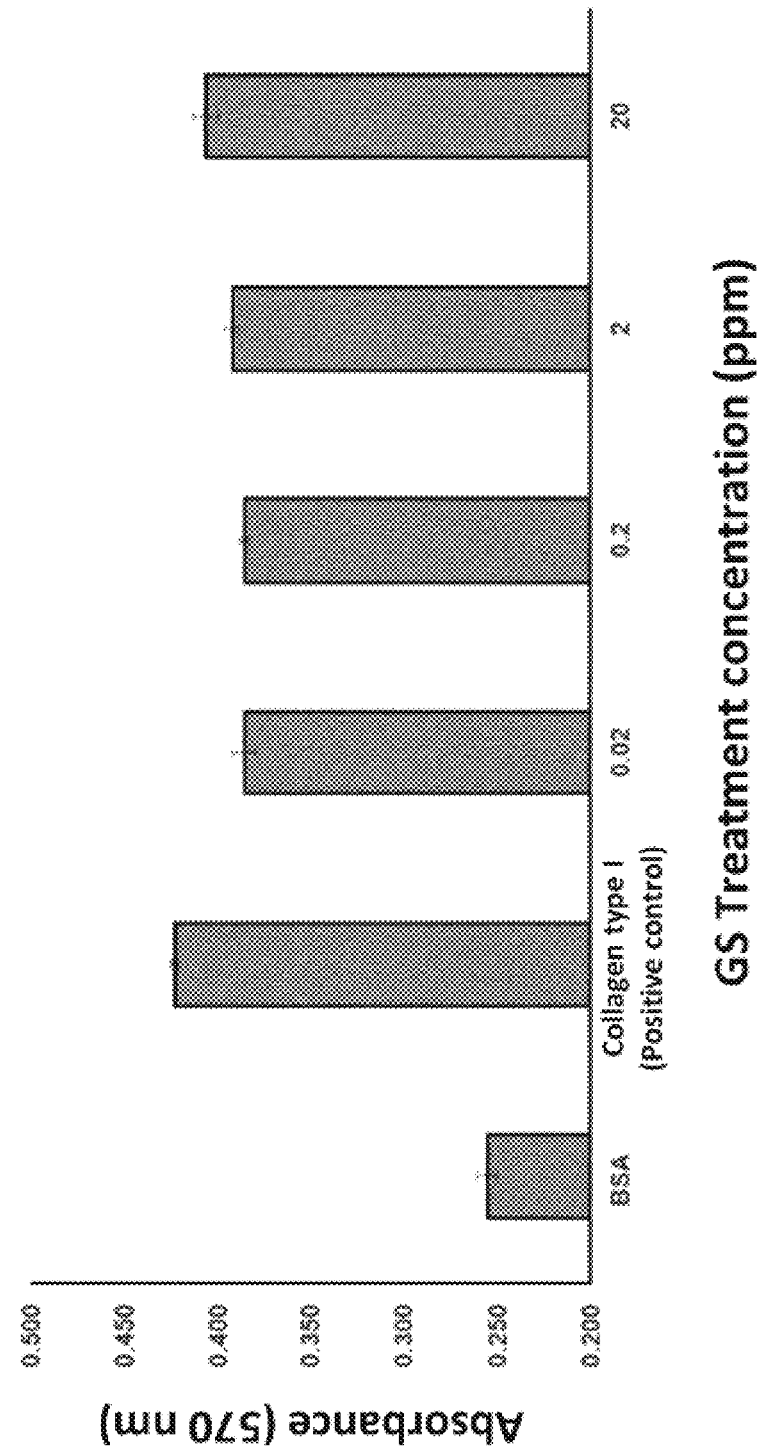
FIG. 8 shows the result of determining the fusion effect between HaCaT cells and the fusion protein after treating HaCaT cells in a multi-well coated with the fusion protein of human growth hormone-spider silk protein.

As a last step, the fusion protein of human growth hormone-spider silk protein (GS) with a concentration of 0, 0.02 ppm, 0.2 ppm, 2 ppm or 20 ppm was coated on a 96-well plate, which was then treated with HaCaT cells followed by culture for 1 day at 37° C. After that, by using PRESTOBLUE™ Cell Viability reagent, the adhesion effect between the cells and fusion protein was analyzed. As a result, it was shown that the HaCaT cells treated with the fusion protein exhibited higher adhesion effect compared to the negative control group which has been treated with BSA (bovine serum albumin). Thus, the adhesion effect of the fusion protein onto a skin cell was shown (FIG. 8).

Experimental Example 1

Skin Wrinkle Improvement, Skin Elasticity Maintaining Effect, and Skin Irritation Sensory Test By using the human growth hormone fusion protein which has been isolated and purified as described in Example 2 as an effective component, cosmetic compositions of Preparation examples 1, 2, 3 and 4 and Comparative examples 1, 2, 3 and 4 were prepared and used for a sensory test.

Specifically, to determine the wrinkle improvement, total 30 men and women with age of 30 or higher but lower than 60 (10 in 30's. 10 in 40's, and 10 in 50's and 60's) as a subject were allowed to apply, once a day for 2 weeks continuously, the composition of Comparative example (i.e., control group) around an eye area at left side of a face or around left side of lips in which many wrinkles are found, or the composition of Preparation example (i.e., test group) around an eye area at right side of a face or around right side of lips. The evaluation was then made based on wrinkle flattening phenomenon around the eye or lips. Furthermore, also for the skin elasticity maintaining effect as one of the functional items described above, the number of days during which skin elasticity is maintained was evaluated according to the same method as described above. Also for the skin irritation item, a sensory test was carried out in terms of itchiness, stingy feeling, and an erythema phenomenon according to the same method as described above. The evaluation was made based on five-point evaluation criteria, i.e., very excellent (5 points), excellent (4 points), moderate (3 points), poor (2 points), and very poor (1 point).

Preparation Example 1 and Comparative Example 1

With or without the addition of the fusion protein of human growth hormone-spider silk protein (GS), a skin composition was prepared with the components and content that are described in the following Table 1.

TABLE 1

Composition of skin cosmetic

| Component | Preparation example 1 (% by weight) | Comparative example 1 (% by weight) |
|---|---|---|
| Human growth hormone fusion protein | 0.01 | — |
| Amino acid stock | 0.1 | 0.1 |
| Mineral mixture | 0.0007 | 0.0007 |
| Purified water | q.s. | q.s. |

The sensory test results of above Preparation example 1 and Comparative example 1 are as shown in the following Table 2.

TABLE 2

Sensory test result of Preparation example 1 and Comparative example 1

Sensory test regarding wrinkle improvement and skin elasticity maintaining effect

| | No. | Wrinkle improvement | | Skin elasticity maintaining | | Skin irritation |
|---|---|---|---|---|---|---|
| | | Preparation example | Comparative example | Preparation example | Comparative example | Preparation example |
| 30's | 1 | 4 | 3 | 5 | 3 | 4 |
| | 2 | 4 | 3 | 4 | 3 | 5 |
| | 3 | 4 | 3 | 4 | 3 | 4 |
| | 4 | 4 | 3 | 3 | 3 | 4 |
| | 5 | 4 | 2 | 4 | 2 | 4 |
| | 6 | 4 | 2 | 4 | 3 | 4 |
| | 7 | 4 | 3 | 5 | 3 | 4 |
| | 8 | 4 | 2 | 4 | 3 | 4 |
| | 9 | 4 | 2 | 4 | 3 | 5 |
| | 10 | 3 | 3 | 4 | 3 | 4 |
| 40's | 11 | 4 | 2 | 5 | 3 | 4 |
| | 12 | 4 | 2 | 5 | 2 | 4 |
| | 13 | 4 | 2 | 4 | 3 | 5 |
| | 14 | 5 | 3 | 5 | 2 | 5 |
| | 15 | 5 | 2 | 4 | 2 | 5 |
| | 16 | 4 | 3 | 4 | 2 | 4 |
| | 17 | 5 | 2 | 5 | 2 | 5 |
| | 18 | 4 | 3 | 5 | 3 | 5 |
| | 19 | 5 | 3 | 4 | 3 | 5 |
| | 20 | 4 | 3 | 5 | 2 | 4 |
| 50's and 60's | 21 | 5 | 2 | 4 | 3 | 5 |
| | 22 | 5 | 2 | 4 | 2 | 5 |
| | 23 | 5 | 2 | 5 | 2 | 5 |
| | 24 | 4 | 3 | 4 | 2 | 5 |
| | 25 | 3 | 2 | 5 | 2 | 4 |
| | 26 | 5 | 3 | 4 | 2 | 4 |
| | 27 | 5 | 2 | 5 | 3 | 5 |
| | 28 | 5 | 2 | 4 | 2 | 5 |
| | 29 | 4 | 2 | 5 | 3 | 5 |
| | 30 | 4 | 2 | 5 | 2 | 4 |
| | Average | 4.2 | 2.4 | 4.4 | 2.5 | 4.5 |

Preparation Example 2 and Comparative Example 2

With or without the addition of the fusion protein of human growth hormone-spider silk protein (GS), an essence composition was prepared with the components and content that are described in the following Table 3.

TABLE 3

Composition of essence cosmetic

| Component | Preparation example 2 (% by weight) | Comparative example 2 (% by weight) |
|---|---|---|
| Human growth hormone fusion protein | 0.01 | — |
| Amino acid stock | 0.05 | 0.05 |
| Mineral mixture | 0.0007 | 0.0007 |
| Glycerol | 5 | 5 |
| 1,3-Butylene glycol | 10 | 10 |
| Carbopol 940 | 0.3 | 0.3 |
| Purified water | q.s. | q.s. |

The sensory test results of above Preparation example 2 and Comparative example 2 are as shown in the following Table 4.

TABLE 4

Sensory test result of Preparation example 2 and Comparative example 2

Sensory test regarding wrinkle improvement and skin elasticity maintaining effect

| | No. | Wrinkle improvement Preparation example | Wrinkle improvement Comparative example | Skin elasticity maintaining Preparation example | Skin elasticity maintaining Comparative example | Skin irritation Preparation example |
|---|---|---|---|---|---|---|
| 30's | 1 | 4 | 2 | 5 | 3 | 4 |
| | 2 | 4 | 2 | 4 | 3 | 5 |
| | 3 | 4 | 3 | 4 | 3 | 4 |
| | 4 | 5 | 2 | 4 | 3 | 4 |
| | 5 | 4 | 2 | 3 | 3 | 4 |
| | 6 | 5 | 2 | 4 | 3 | 4 |
| | 7 | 4 | 3 | 4 | 3 | 4 |
| | 8 | 5 | 2 | 5 | 3 | 4 |
| | 9 | 4 | 2 | 5 | 2 | 5 |
| | 10 | 4 | 3 | 4 | 3 | 4 |
| 40's | 11 | 5 | 2 | 5 | 2 | 5 |
| | 12 | 4 | 3 | 4 | 2 | 5 |
| | 13 | 4 | 2 | 5 | 2 | 5 |
| | 14 | 5 | 3 | 5 | 2 | 5 |
| | 15 | 5 | 2 | 5 | 2 | 5 |
| | 16 | 5 | 2 | 4 | 2 | 4 |
| | 17 | 5 | 2 | 5 | 2 | 5 |
| | 18 | 4 | 3 | 5 | 3 | 5 |
| | 19 | 5 | 2 | 4 | 2 | 5 |
| | 20 | 4 | 3 | 5 | 2 | 5 |
| 50's and 60's | 21 | 5 | 2 | 4 | 2 | 5 |
| | 22 | 5 | 2 | 5 | 2 | 5 |
| | 23 | 5 | 2 | 5 | 2 | 5 |
| | 24 | 4 | 2 | 5 | 2 | 5 |
| | 25 | 5 | 2 | 4 | 3 | 5 |
| | 26 | 5 | 3 | 5 | 2 | 4 |
| | 27 | 5 | 2 | 5 | 3 | 5 |
| | 28 | 5 | 2 | 4 | 2 | 5 |
| | 29 | 4 | 2 | 5 | 3 | 5 |
| | 30 | 5 | 1 | 5 | 2 | 4 |
| | Average | 4.5 | 2.2 | 4.5 | 2.4 | 4.6 |

Preparation Example 3 and Comparative Example 3

With or without the addition of the fusion protein of human growth hormone-spider silk protein (GS), a lotion composition was prepared with the components and content that are described in the following Table 5.

TABLE 5

Composition of lotion cosmetic

| Component | Preparation example 3 (% by weight) | Comparative example 3 (% by weight) |
|---|---|---|
| Human growth hormone fusion protein | 0.01 | — |
| Amino acid stock | 0.05 | 0.05 |
| Mineral mixture | 0.0007 | 0.0007 |
| Glycerol | 3 | 3 |
| 1,3-Butylene glycol | 10 | 10 |
| Mineral oil | 5 | 5 |
| Cetyl alcohol | 2 | 2 |
| Xanthan gum | 0.5 | 0.5 |
| Purified water | q.s. | q.s. |

The sensory test results of above Preparation example 3 and Comparative example 3 are as shown in the following Table 6.

TABLE 6

Sensory test result of Preparation example 3 and Comparative example 3

Sensory test regarding wrinkle improvement and skin elasticity maintaining effect

| | No. | Wrinkle improvement Preparation example | Wrinkle improvement Comparative example | Skin elasticity maintaining Preparation example | Skin elasticity maintaining Comparative example | Skin irritation Preparation example |
|---|---|---|---|---|---|---|
| 30's | 1 | 4 | 2 | 5 | 3 | 5 |
| | 2 | 4 | 2 | 4 | 2 | 5 |
| | 3 | 4 | 3 | 4 | 3 | 4 |
| | 4 | 3 | 2 | 4 | 3 | 4 |
| | 5 | 4 | 2 | 4 | 3 | 4 |
| | 6 | 3 | 2 | 4 | 2 | 4 |
| | 7 | 4 | 3 | 5 | 3 | 5 |
| | 8 | 4 | 2 | 4 | 3 | 4 |
| | 9 | 4 | 2 | 5 | 2 | 5 |
| | 10 | 4 | 2 | 4 | 2 | 4 |
| 40's | 11 | 5 | 2 | 5 | 2 | 5 |
| | 12 | 5 | 3 | 5 | 2 | 5 |
| | 13 | 5 | 2 | 5 | 2 | 5 |
| | 14 | 5 | 2 | 5 | 2 | 5 |
| | 15 | 5 | 2 | 5 | 1 | 5 |
| | 16 | 5 | 1 | 4 | 2 | 4 |
| | 17 | 5 | 2 | 5 | 2 | 5 |
| | 18 | 5 | 3 | 4 | 3 | 5 |
| | 19 | 5 | 2 | 5 | 1 | 5 |
| | 20 | 5 | 1 | 5 | 2 | 5 |
| 50's and 60's | 21 | 5 | 2 | 4 | 2 | 5 |
| | 22 | 5 | 2 | 5 | 2 | 5 |
| | 23 | 5 | 2 | 4 | 2 | 5 |
| | 24 | 4 | 2 | 4 | 2 | 5 |
| | 25 | 4 | 2 | 4 | 1 | 5 |
| | 26 | 5 | 3 | 4 | 2 | 4 |
| | 27 | 4 | 2 | 4 | 3 | 5 |
| | 28 | 5 | 2 | 5 | 2 | 5 |
| | 29 | 5 | 2 | 4 | 3 | 5 |
| | 30 | 5 | 1 | 5 | 1 | 5 |
| | Average | 4.5 | 2.0 | 4.4 | 2.1 | 4.7 |

Preparation Example 4 and Comparative Example 4

With or without the addition of the fusion protein of human growth hormone-spider silk protein (GS), a crème composition was prepared with the components and content that are described in the following Table 7.

TABLE 7

Composition of creme cosmetic

| Component | Preparation example 4 (% by weight) | Comparative example 4 (% by weight) |
|---|---|---|
| Human growth hormone fusion protein | 0.01 | — |
| Amino acid stock | 0.05 | 0.05 |
| Mineral mixture | 0.0007 | 0.0007 |
| Glycerol | 2 | 2 |
| Mineral oil | 10 | 10 |
| Olive emulsion wax | 3 | 3 |
| Cetyl alcohol | 2 | 2 |
| Purified water | q.s. | q.s. |

The sensory test results of above Preparation example 4 and Comparative example 4 are as shown in the following Table 8.

TABLE 8

Sensory test result of Preparation example 4 and Comparative example 4

| | | Sensory test regarding wrinkle improvement and skin elasticity maintaining effect | | | | |
|---|---|---|---|---|---|---|
| | | Wrinkle improvement | | Skin elasticity maintaining | | Skin irritation |
| | No. | Preparation example | Comparative example | Preparation example | Comparative example | Preparation example |
| 30's | 1 | 4 | 3 | 4 | 2 | 5 |
| | 2 | 4 | 2 | 5 | 2 | 5 |
| | 3 | 4 | 3 | 4 | 2 | 4 |
| | 4 | 4 | 2 | 5 | 3 | 4 |
| | 5 | 4 | 3 | 4 | 3 | 4 |
| | 6 | 4 | 2 | 4 | 2 | 4 |
| | 7 | 4 | 3 | 4 | 3 | 5 |
| | 8 | 4 | 2 | 5 | 3 | 4 |
| | 9 | 5 | 2 | 4 | 2 | 5 |
| | 10 | 4 | 3 | 4 | 2 | 4 |
| 40's | 11 | 5 | 3 | 5 | 2 | 5 |
| | 12 | 5 | 3 | 5 | 2 | 5 |
| | 13 | 5 | 2 | 4 | 2 | 5 |
| | 14 | 5 | 2 | 4 | 2 | 5 |
| | 15 | 5 | 2 | 5 | 3 | 5 |
| | 16 | 5 | 2 | 4 | 2 | 4 |
| | 17 | 5 | 2 | 5 | 2 | 5 |
| | 18 | 4 | 3 | 5 | 3 | 5 |
| | 19 | 5 | 2 | 5 | 2 | 5 |
| | 20 | 5 | 2 | 4 | 2 | 5 |
| 50's and 60's | 21 | 5 | 2 | 3 | 2 | 5 |
| | 22 | 5 | 2 | 4 | 2 | 5 |
| | 23 | 4 | 2 | 5 | 2 | 5 |
| | 24 | 4 | 2 | 3 | 2 | 5 |
| | 25 | 3 | 2 | 4 | 2 | 5 |
| | 26 | 4 | 3 | 5 | 2 | 4 |
| | 27 | 4 | 2 | 4 | 3 | 5 |
| | 28 | 3 | 2 | 5 | 2 | 5 |
| | 29 | 4 | 2 | 4 | 3 | 5 |
| | 30 | 4 | 2 | 4 | 2 | 5 |
| | Average | 4.3 | 2.2 | 4.3 | 2.2 | 4.7 |

A sequence listing electronically submitted with the present application on Jul. 14, 2020 as an ASCII text file named 20200714_Q34520_GR08_TU_SEQ, created on Jul. 14, 2020 and having a size of 13,000 bytes, is incorporated herein by reference in its entirety.

What is claimed is:

1. A human growth hormone fusion protein having comprising the amino acid sequence of SEQ ID NO: 3 or SEQ ID NO: 4.

2. The human growth fusion protein of claim 1, comprising the amino acid sequence of SEQ ID NO: 3.

3. The human growth fusion protein of claim 1, comprising the amino acid sequence of SEQ ID NO: 4.

4. A cosmetic composition comprising, as an effective component, a human growth hormone fusion protein comprising the amino acid sequence of SEQ ID NO: 3 or SEQ ID NO: 4, wherein an amount of the human growth hormone fusion protein is in the range of 0.00001 to 0.002% by weight relative to the total weight of the cosmetic composition.

5. The cosmetic composition of claim 4, wherein the cosmetic composition comprises any one formulation selected from the group consisting of a skin softener, a skin toner, an astringent, a lotion, a milk lotion, a moisture lotion, a nutrition lotion, a massage crème, a nutrition crème, an eye crème, a moisture crème, a hand crème, an essence, a nutrition essence, a pack, a cleansing foam, a cleansing water, a cleansing lotion, a cleansing crème, a body lotion, a body cleanser, a soap, and a powder.

* * * * *

SEQUENCE LISTING

<160> NUMBER OF SEQ ID NOS: 14

<210> SEQ ID NO 1
<211> LENGTH: 105
<212> TYPE: PRT
<213> ORGANISM: Artificial Sequence
<220> FEATURE:
<223> OTHER INFORMATION: spider silk protein

<400> SEQUENCE: 1

Gln Gly Ala Gly Ala Ala Ala Ala Ala Ala Gly Gly Ala Gly Gly Gly
1               5                   10                  15

Gly Gln Gly Gly Tyr Gly Gly Gln Gly Ala Gly Ala Ala Ala Ala Ala
                20                  25                  30

Ala Gly Gly Ala Gly Gly Gly Gly Gln Gly Gly Tyr Gly Gly Gln Gly
            35                  40                  45

Ala Gly Ala Ala Ala Ala Ala Ala Gly Gly Ala Gly Gly Gly Gly Gln
        50                  55                  60

Gly Gly Tyr Gly Gly Gln Gly Ala Gly Ala Ala Ala Ala Ala Ala Gly
65                  70                  75                  80

Gly Ala Gly Gly Gly Gly Gln Gly Gly Tyr Gly Gly Ala Ala Ala Ala
                85                  90                  95

Ala Ala Gly Gly Ala Gly Gly Gly
            100                 105

<210> SEQ ID NO 2
<211> LENGTH: 191
<212> TYPE: PRT
<213> ORGANISM: Homo sapiens

<400> SEQUENCE: 2

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
                35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
                115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
                180                 185                 190

<210> SEQ ID NO 3
<211> LENGTH: 305
<212> TYPE: PRT
<213> ORGANISM: Artificial Sequence
<220> FEATURE:
<223> OTHER INFORMATION: spider silk protein-human growth hormone fusion
      protein

<400> SEQUENCE: 3

Met Gln Gly Ala Gly Ala Ala Ala Ala Ala Gly Gly Ala Gly Gly Gly
1               5                   10                  15

Gly Gly Gln Gly Gly Tyr Gly Gly Gln Gly Ala Gly Ala Ala Ala Ala
                20                  25                  30

Ala Ala Gly Gly Ala Gly Gly Gly Gly Gln Gly Gly Tyr Gly Gly Gln
                35                  40                  45

Gly Ala Gly Ala Ala Ala Ala Ala Gly Gly Ala Gly Gly Gly Gly Gly
    50                  55                  60

Gln Gly Gly Tyr Gly Gly Gln Gly Ala Gly Ala Ala Ala Ala Ala Ala
65                  70                  75                  80

Gly Gly Ala Gly Gly Gly Gln Gly Gly Tyr Gly Gly Ala Gly Ala Ala
                85                  90                  95

Ala Ala Ala Gly Gly Ala Gly Gly Gly Phe Pro Thr Ile Pro Leu
                100                 105                 110

Ser Arg Leu Phe Asp Asn Ala Met Leu Arg Ala His Arg Leu His Gln
                115                 120                 125

Leu Ala Phe Asp Thr Tyr Gln Glu Phe Glu Glu Ala Tyr Ile Pro Lys
                130                 135                 140

Glu Gln Lys Tyr Ser Phe Leu Gln Asn Pro Gln Thr Ser Leu Cys Phe
145                 150                 155                 160

Ser Glu Ser Ile Pro Thr Pro Ser Asn Arg Glu Glu Thr Gln Gln Lys
                165                 170                 175

Ser Asn Leu Glu Leu Leu Arg Ile Ser Leu Leu Leu Ile Gln Ser Trp
                180                 185                 190

Leu Glu Pro Val Gln Phe Leu Arg Ser Val Phe Ala Asn Ser Leu Val

```
                195                 200                 205
Tyr Gly Ala Ser Asp Ser Asn Val Tyr Asp Leu Leu Lys Asp Leu Glu
            210                 215                 220

Glu Gly Ile Gln Thr Leu Met Gly Arg Leu Glu Asp Gly Ser Pro Arg
225                 230                 235                 240

Thr Gly Gln Ile Phe Lys Gln Thr Tyr Ser Lys Phe Asp Thr Asn Ser
                245                 250                 255

His Asn Asp Asp Ala Leu Leu Lys Asn Tyr Gly Leu Leu Tyr Cys Phe
            260                 265                 270

Arg Lys Asp Met Asp Lys Val Glu Thr Phe Leu Arg Ile Val Gln Cys
        275                 280                 285

Arg Ser Val Glu Gly Ser Cys Gly Phe Leu Glu His His His His
    290                 295                 300

His
305

<210> SEQ ID NO 4
<211> LENGTH: 305
<212> TYPE: PRT
<213> ORGANISM: Artificial Sequence
<220> FEATURE:
<223> OTHER INFORMATION: human growth hormone-spider silk protein fusion
      protein

<400> SEQUENCE: 4

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Arg Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

Gln Gly Ala Gly Ala Ala Ala Ala Ala Ala Gly Gly Ala Gly Gly Gly
        195                 200                 205

Gly Gln Gly Gly Tyr Gly Gly Gln Gly Ala Gly Ala Ala Ala Ala Ala
    210                 215                 220

Ala Gly Gly Ala Gly Gly Gly Gly Gln Gly Gly Tyr Gly Gly Gln Gly
225                 230                 235                 240
```

```
Ala Gly Ala Ala Ala Ala Ala Gly Gly Ala Gly Gly Gly Gln
            245                 250                 255

Gly Gly Tyr Gly Gly Gln Gly Ala Ala Ala Ala Ala Gly
        260             265             270

Gly Ala Gly Gly Gly Gln Gly Tyr Gly Gly Ala Ala Ala
    275             280             285

Ala Ala Gly Gly Ala Gly Gly Gly Leu Glu His His His His
    290             295             300

His
305
```

<210> SEQ ID NO 5
<211> LENGTH: 915
<212> TYPE: DNA
<213> ORGANISM: Artificial Sequence
<220> FEATURE:
<223> OTHER INFORMATION: spider silk protein-human growth hormone fusion protein

<400> SEQUENCE: 5

```
atgcagggcg cgggcgcggc ggcggcggcg gcgggcggcg cgggcggcgg cggccagggc      60
ggctatggcg gccagggcgc gggcgcggcg gcggcggcgg cgggcggcgc gggcggcggc     120
ggccagggcg gctatggcgg ccagggcgcg gcgcggcgg cggcggcggc gggcggcgcg     180
ggcggcggcg gccagggcgg ctatggcggc cagggcgcgg gcgcggcggc ggcggcggcg     240
ggcggcgcgg gcggcggcgg ccagggcggc tatggcggcg cggcggcggc ggcggcgggc     300
ggcgcgggcg gcggcggctt ccgaccatt ccgctgagcc gcctgtttga taacgcgatg     360
ctgcgcgcgc atcgcctgca tcagctggcg tttgatacct atcaggaatt tgaagaagcg     420
tatattccga agaacagaa atatagcttt ctgcagaacc gcagaccag cctgtgcttt      480
agcgaaagca ttccgacccc gagcaaccgc gaagaaaccc agcagaaaag caacctggaa     540
ctgctgcgca ttagcctgct gctgattcag agctggctgg aaccggtgca gtttctgcgc     600
agcgtgtttg cgaacagcct ggtgtatggc gcgagcgata gcaacgtgta tgatctgctg     660
aaagatctgg aagaaggcat tcagaccctg atgggccgcc tggaagatgg cagcccgcgc     720
accggccaga tttttaaaca gacctatagc aaatttgata ccaacagcca taacgatgat     780
gcgctgctga aaaactatgg cctgctgtat tgctttcgca agatatgga taaagtggaa     840
acctttctgc gcattgtgca gtgccgcagc gtggaaggca gctgcggctt ctgtgaacat     900
catcatcatc atcat                                                      915
```

<210> SEQ ID NO 6
<211> LENGTH: 915
<212> TYPE: DNA
<213> ORGANISM: Artificial Sequence
<220> FEATURE:
<223> OTHER INFORMATION: human growth hormone-spider silk protein fusion protein

<400> SEQUENCE: 6

```
atgtttccga ccattccgct gagccgcctg tttgataacg cgatgctgcg cgcgcatcgc      60
ctgcatcagc tggcgtttga tacctatcag gaatttgaag aagcgtatat tccgaaagaa     120
cagaaatata gctttctgca gaacccgcag accagcctgt gctttagcga aagcattccg     180
accccgagca accgcgaaga aacccagcag aaaagcaacc tggaactgct gcgcattagc     240
ctgctgctga ttcagagctg gctggaaccg gtgcagtttc tgcgcagcgt gtttgcgaac     300
```

-continued

| | | | | |
|---|---|---|---|---|
| agcctggtgt | atggcgcgag | cgatagcaac | gtgtatgatc | tgctgaaaga tctggaagaa | 360 |
| ggcattcaga | ccctgatggg | ccgcctggaa | gatggcagcc | cgcgcaccgg ccagattttt | 420 |
| aaacagacct | atagcaaatt | tgataccaac | agccataacg | atgatgcgct gctgaaaaac | 480 |
| tatggcctgc | tgtattgctt | tcgcaaagat | atggataaag | tggaaacctt tctgcgcatt | 540 |
| gtgcagtgcc | gcagcgtgga | aggcagctgc | ggctttcagg | gcgcgggcgc ggcggcggcg | 600 |
| gcggcgggcg | gcgcgggcgg | cggcggccag | ggcggctatg | gcggcagggg cgcgggcgcg | 660 |
| gcggcggcgg | cggcgggcgg | cgcgggcggc | ggcggccagg | gcggctatgg cggccagggc | 720 |
| gcgggcgcgg | cggcggcggc | ggcgggcggc | gcgggcggcg | gcggccaggg cggctatggc | 780 |
| ggccagggcg | cgggcgcggc | ggcggcggcg | gcgggcggcg | cggcggcgg cggccagggc | 840 |
| ggctatggcg | gcgcggcggc | ggcggcggcg | ggcggcgcgg | gcggcggcgg cctggaacat | 900 |
| catcatcatc | atcat | | | | 915 |

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
aaggagatat acatatgcaa ggtgctggtg ctgccg    36

<210> SEQ ID NO 8
<211> LENGTH: 36
<212> TYPE: DNA
<213> ORGANISM: Artificial Sequence
<220> FEATURE:
<223> OTHER INFORMATION: primer

<400> SEQUENCE: 8
cagcggaata gtggggaatg cgcctgctcc ctgtcc    36

<210> SEQ ID NO 9
<211> LENGTH: 36
<212> TYPE: DNA
<213> ORGANISM: Artificial Sequence
<220> FEATURE:
<223> OTHER INFORMATION: primer

<400> SEQUENCE: 9
ggacagggag caggcgcatt ccccactatt ccgctg    36

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
ggtggtggtg ctcgagaaag ccgcaggaac cctcg    35

<210> SEQ ID NO 11
<211> LENGTH: 32
<212> TYPE: DNA
<213> ORGANISM: Artificial Sequence
<220> FEATURE:
<223> OTHER INFORMATION: primer

<400> SEQUENCE: 11

```
aaggagatat acatatgttc cccactattc cg                               32

<210> SEQ ID NO 12
<211> LENGTH: 38
<212> TYPE: DNA
<213> ORGANISM: Artificial Sequence
<220> FEATURE:
<223> OTHER INFORMATION: primer

<400> SEQUENCE: 12
cggcagcacc agcaccttga aagccgcagg aaccctcg                         38

<210> SEQ ID NO 13
<211> LENGTH: 38
<212> TYPE: DNA
<213> ORGANISM: Artificial Sequence
<220> FEATURE:
<223> OTHER INFORMATION: primer

<400> SEQUENCE: 13
cgagggttcc tgcggctttc aaggtgctgg tgctgccg                         38

<210> SEQ ID NO 14
<211> LENGTH: 34
<212> TYPE: DNA
<213> ORGANISM: Artificial Sequence
<220> FEATURE:
<223> OTHER INFORMATION: primer

<400> SEQUENCE: 14
ggtggtggtg ctcgagtgcg cctgctccct gtcc                             34
```